US009377389B2

(12) United States Patent
Parrington

(10) Patent No.: US 9,377,389 B2
(45) Date of Patent: Jun. 28, 2016

(54) IMPACTION DENSITOMETER

(71) Applicant: United States Department of Energy, Washington, DC (US)

(72) Inventor: Josef R. Parrington, Rexford, NY (US)

(73) Assignee: U.S. Department of Energy, Washington, DC (US)

( * ) Notice: Subject to any disclaimer, the term of this patent is extended or adjusted under 35 U.S.C. 154(b) by 360 days.

(21) Appl. No.: 14/186,057

(22) Filed: Feb. 21, 2014

(65) Prior Publication Data

US 2014/0238125 A1 Aug. 28, 2014

Related U.S. Application Data

(60) Provisional application No. 61/768,798, filed on Feb. 25, 2013.

(51) Int. Cl.
  *G01N 15/10* (2006.01)
  *G01N 15/14* (2006.01)
  *G01N 9/00* (2006.01)
  *G01N 9/02* (2006.01)

(52) U.S. Cl.
  CPC ............. *G01N 15/1463* (2013.01); *G01N 9/00* (2013.01); *G01N 9/02* (2013.01); *G01N 15/10* (2013.01); *G01N 2009/022* (2013.01); *G01N 2015/1493* (2013.01); *G01N 2015/1497* (2013.01)

(58) Field of Classification Search
  CPC .................. G01N 2015/1445; G01N 15/1463; G01N 15/1493; G01N 15/1497; G01N 2015/1043; G01N 2015/1075
  See application file for complete search history.

(56) References Cited

U.S. PATENT DOCUMENTS 7,126,694 B1 * 10/2006 Bachalo ............. G01N 15/1459
  356/28.5

OTHER PUBLICATIONS

Nilsson, C.S., et al. "Measured Velocities of Interplanetary Dust Particles from OGO-1", Smithsonian Contributions to Astrophysics, vol. 11, 1967.*

* cited by examiner

*Primary Examiner* — Paul West
(74) *Attorney, Agent, or Firm* — Robert T. Burns; John T. Lucas

(57) ABSTRACT

Disclosed is an impaction densitometer having a chamber configured to receive a particle; a beam generator configured to emit a beam; a detector configured to receive the beam and convert a change in intensity of the received beam into an electrical signal corresponding to a particle volume; an impact sensor positioned a known distance from the beam and configured to measure a particle momentum as a function of an impact energy transferred from the particle to the impact sensor; a velocity calculator configured to calculate a particle velocity based on a time it takes the particle to pass through the beam and strike the impact sensor; a mass calculator configured to calculate a particle mass as a function of the particle momentum and velocity; and a density calculator configured to calculate a particle density as a function of the particle mass and volume.

20 Claims, 6 Drawing Sheets

IMPACTION DENSITOMETER

NOTICE OF GOVERNMENT RIGHTS

The United States Government has rights in this application and any resultant patents claiming priority to this application pursuant to contract DE-AC12-00SN39357 between the United States Department of Energy and Bechtel Marine Propulsion Corporation Knolls Atomic Power Laboratory.

TECHNOLOGICAL FIELD

The present subject matter relates to density measurement.

BACKGROUND

An important parameter for the characterization of particulate substances is density. Measuring individual particle density becomes problematic, however, as particle size decreases. While optical and other measurement devices exist to determine overall sample sizes or volumes, these devices have difficulty measuring individual particle sizes. Moreover, measurement techniques often obtain only aggregate particle sizes, allowing at best an estimate or average of individual particle sizes. Obtaining an individual particle mass is also problematic, which in turn makes obtaining particle density problematic. Microbalances exist to obtain individual particle masses, but they are relatively costly and slow, often taking minutes to obtain the mass of even a single particle. Mercury pycnometery is often used to determine density of small particles, but can only obtain an average particle density. It cannot produce a histogram of individual particle densities. It also requires several grams of sample material, is labor intensive, and uses mercury, a hazardous substance.

BRIEF SUMMARY

Disclosed is an impaction densitometer having a chamber configured to receive a particle; a beam generator configured to emit a beam crossing a particle direction of travel within the chamber; a detector configured to receive the beam and convert a change in intensity of the received beam, resulting from the particle passing through the beam, into an electrical signal corresponding to a particle volume; an impact sensor positioned a known distance from the beam and configured to measure a particle momentum as a function of an impact energy transferred from the particle to the impact sensor; a velocity calculator configured to calculate a particle velocity based on a time it takes the particle to pass through the beam and strike the impact sensor; a mass calculator configured to calculate a particle mass as a function of the particle momentum and velocity; and a density calculator configured to calculate a particle density as a function of the particle mass and volume.

Also disclosed is a method of particle measurement, including the steps of passing a particle through a beam; measuring a change in intensity of the beam resulting from the particle passing through the beam; calculating a particle volume based on the change in beam intensity; impacting the particle at a known distance from the beam; measuring an impact energy of the particle; calculating a particle momentum as a function of the particle impact energy; calculating a particle velocity as a function of a time it takes the particle to impact after travelling the known distance from the beam; calculating a particle mass as a function of the particle momentum and velocity; and calculating a particle density as a function of the particle mass and volume. Certain exemplary methods include the step of calculating at least ten particle densities per second, and still other exemplary methods include the step of preparing a histogram of at least one of a plurality of particle densities and a plurality of particle sizes.

In yet another exemplary embodiment, a computer program product comprising a non-transitory computer readable medium having stored thereon computer executable instructions that when executed causes the computer to perform a method of particle measurement, the method comprising the steps of passing a particle through a beam; measuring a change in intensity of the beam resulting from the particle passing through the beam; calculating a particle volume based on the change in beam intensity; impacting the particle at a known distance from the beam; measuring an impact energy of the particle; calculating a particle momentum as a function of the particle impact energy; calculating a particle velocity as a function of a time it takes the particle to impact after passing through the known distance from the beam; calculating a particle mass as a function of the particle momentum and velocity; and calculating a particle density as a function of the particle mass and volume.

BRIEF DESCRIPTION OF THE DRAWINGS

A description of the present subject matter including various embodiments thereof is presented with reference to the accompanying drawings, the description not meaning to be considered limiting in any matter, wherein.

Similar reference numerals and designators in the various figures refer to like elements.

DETAILED DESCRIPTION

Figure 1A:
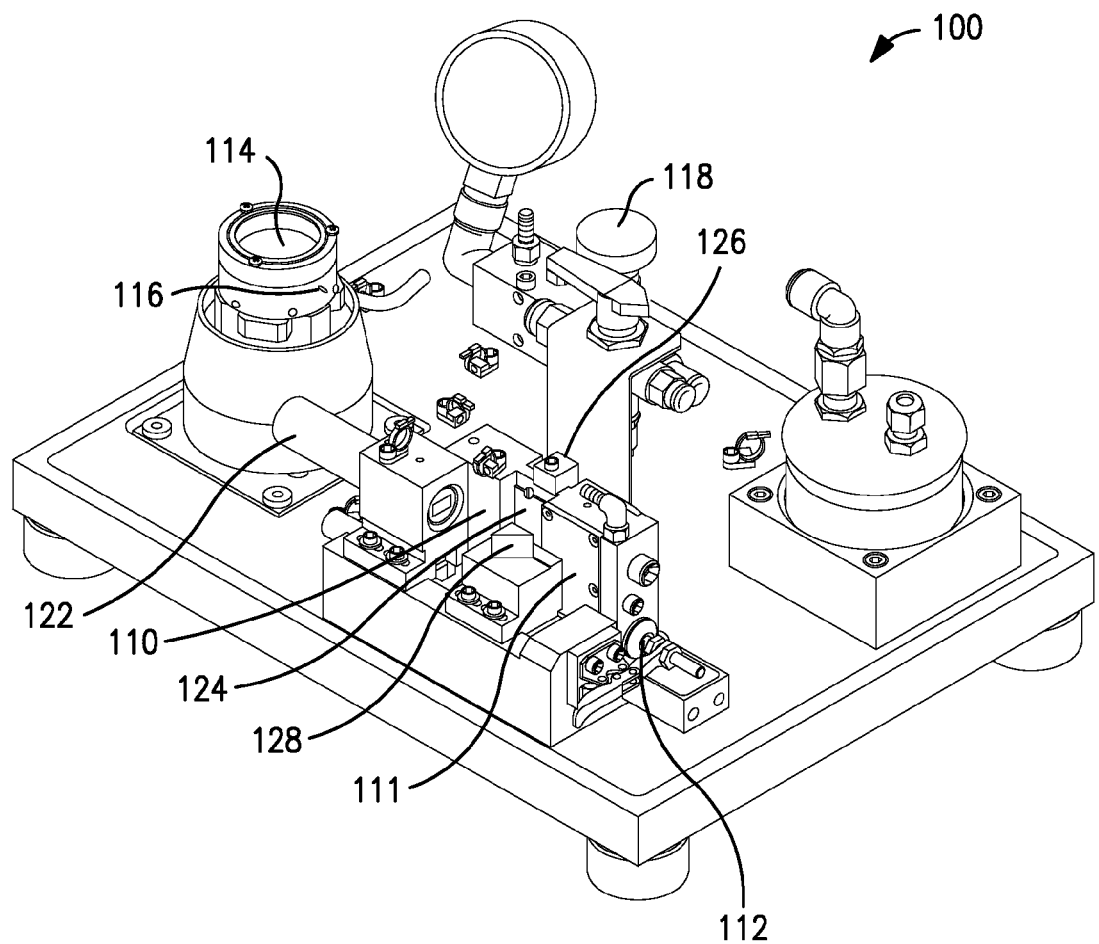
FIGS. 1A-1D illustrate selected views of an exemplary embodiment of an impaction densitometer.
Figure 1B:
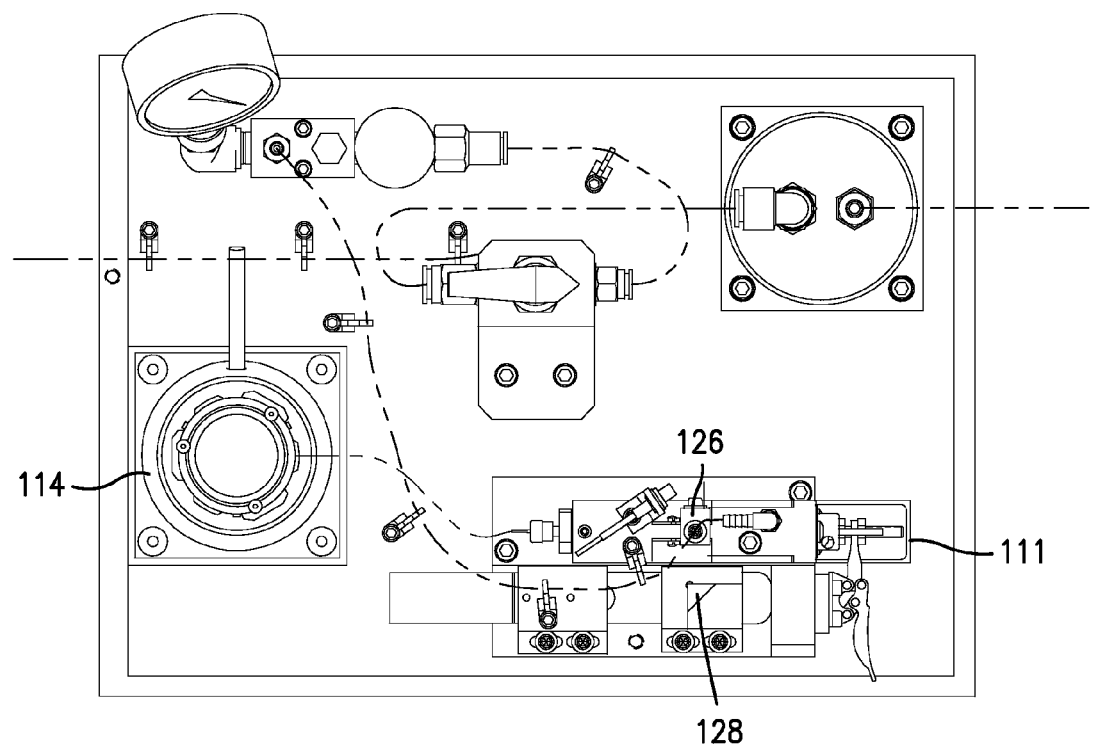
Figure 1B:
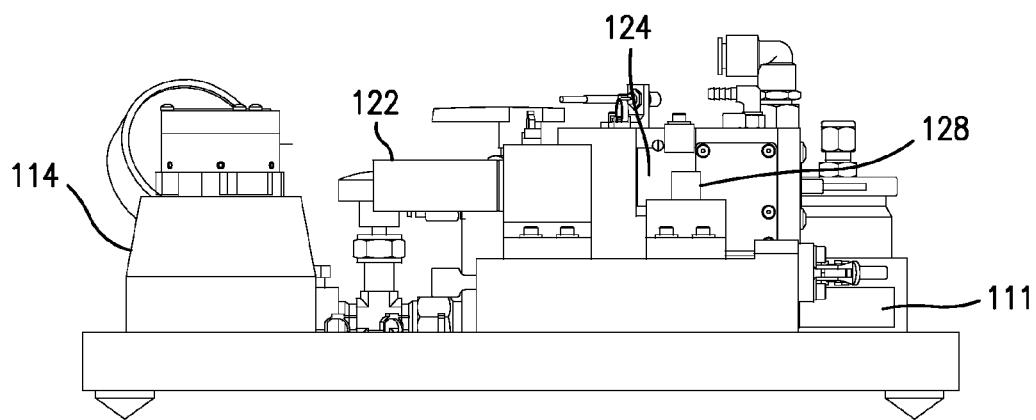
Figure 1C:
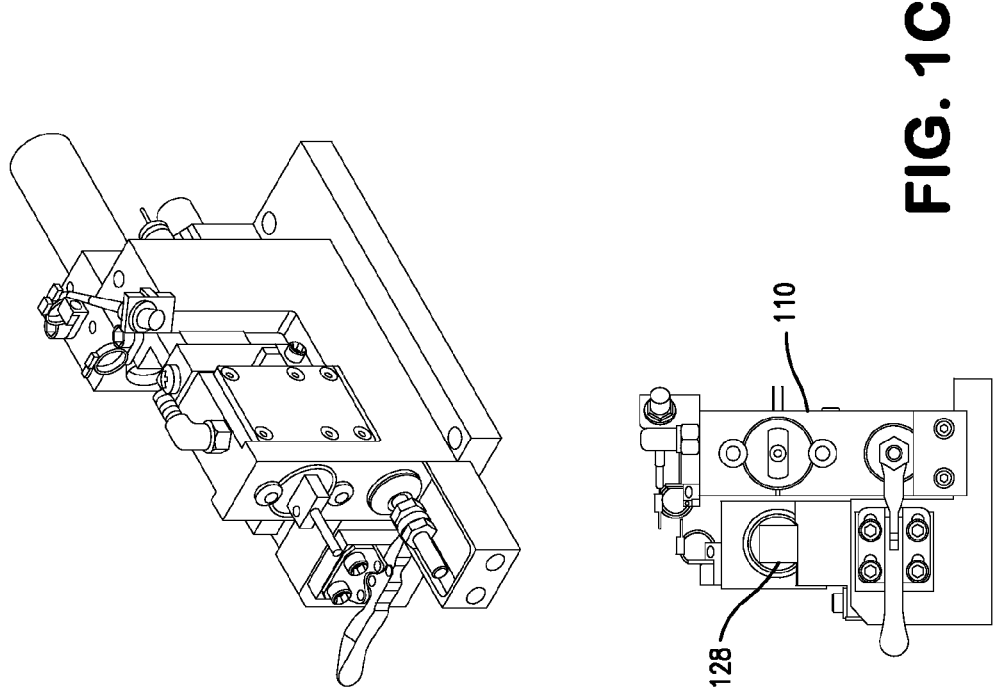
Figure 1C:
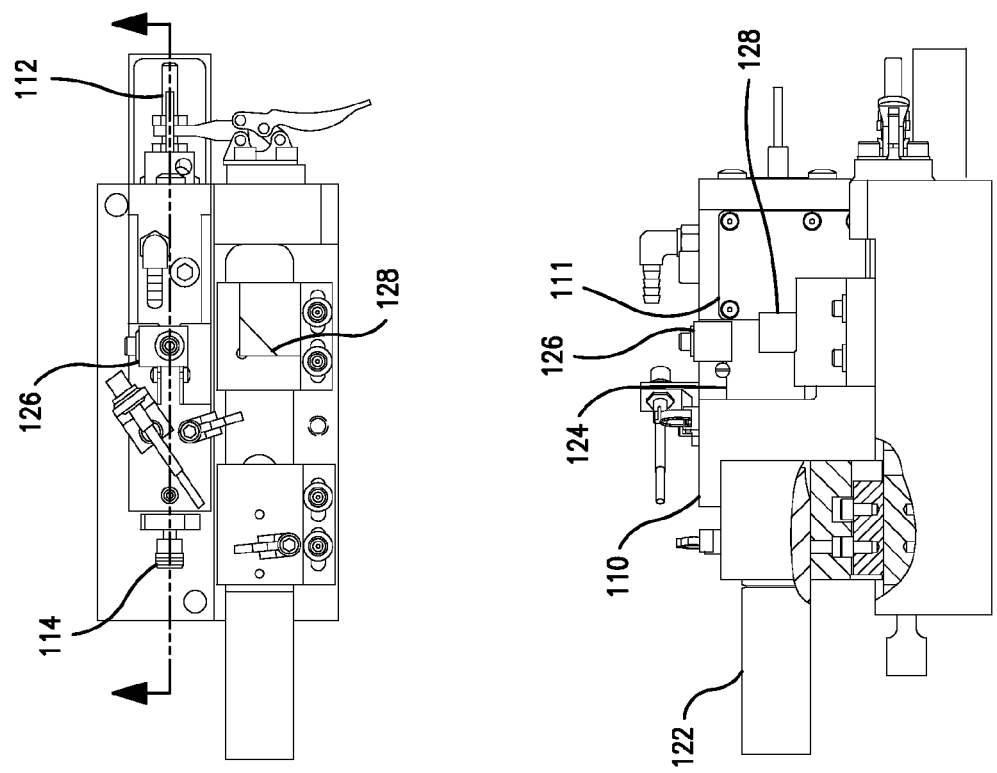
Figure 1D:
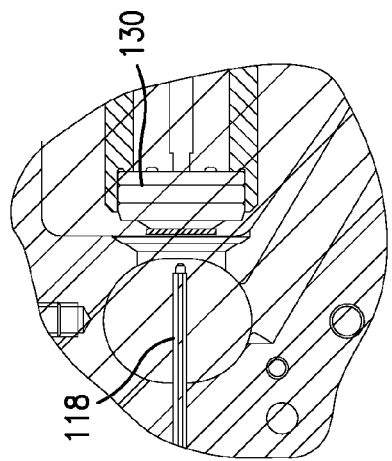
Figure 1D:
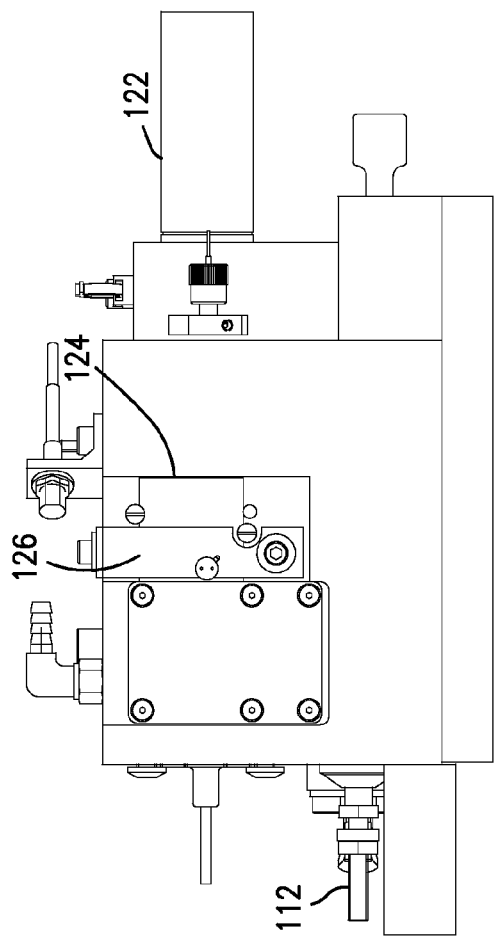
Figure 1D:
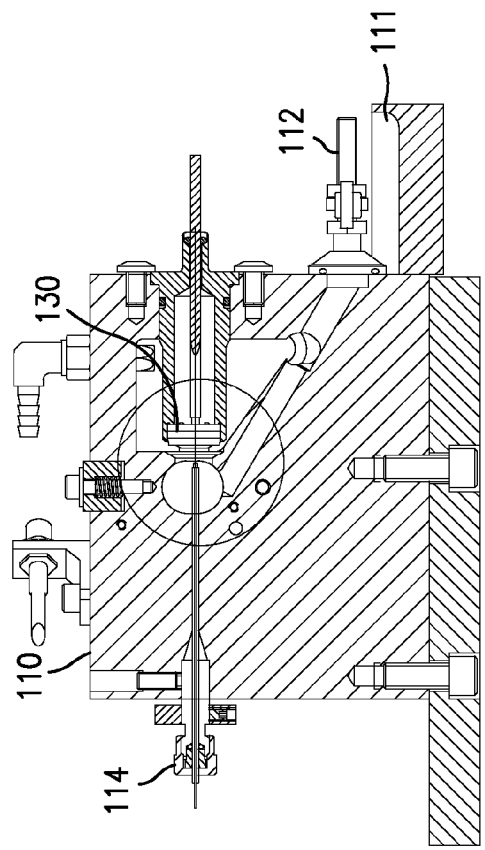
Figure 1E:
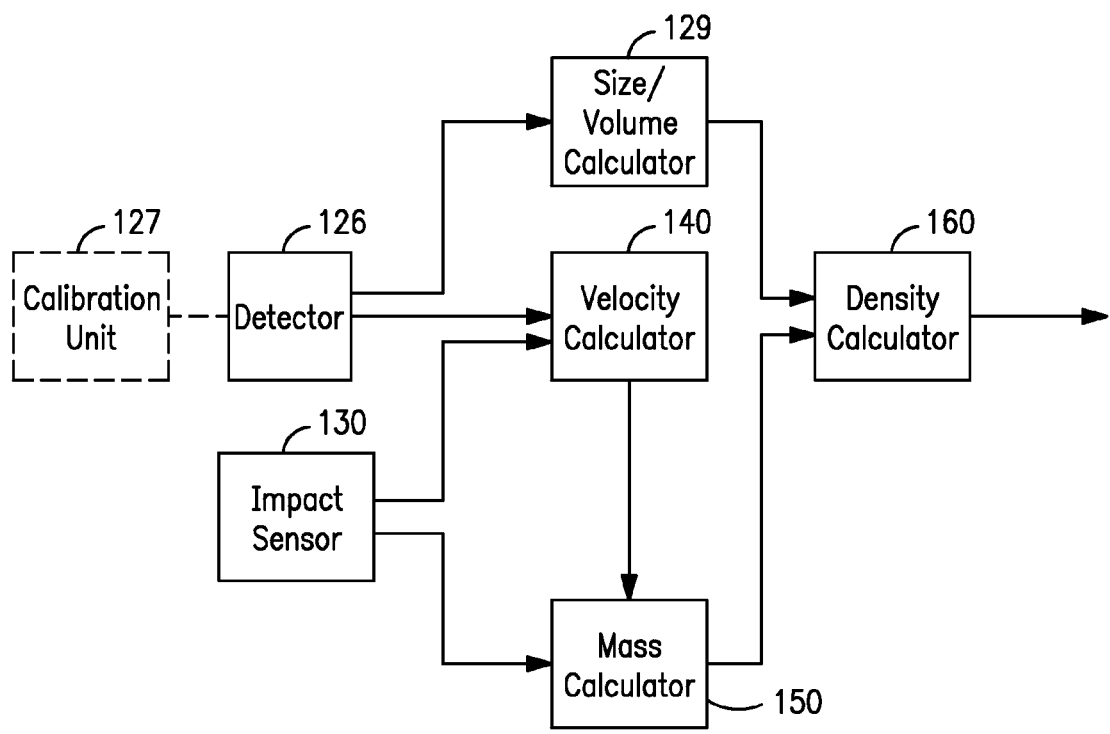
FIG. 1E illustrates a block diagram of portions of an exemplary embodiment of an impaction densitometer.

FIGS. 1A-1D illustrate selected views of an exemplary embodiment of an impaction densitometer 100, and FIG. 1E illustrates a block diagram of portions of an exemplary embodiment of an impaction densitometer 100. The impaction densitometer 100 provides information including, but not limited to, individual particle density, sample density distribution, and average particle density. In certain embodiments, data acquisition is computerized, with data acquisition rates of up to approximately ten particle densities per second, for example. In certain exemplary embodiments, particles smaller than 1/32" in diameter are measured from a sample of approximately 1/10th of a gram. In certain exemplary embodiments, a sample size is 500 to 1000 particles ranging in size between 50 and 1000 microns, which are measured in the span of a few minutes. Other techniques often take much longer to obtain measurements for the same number of samples, and even then only measure an overall sample density rather than individual particle densities. If mercury pycnometry were used, for example, a sample size of two to five grams would be required, only average particle density would be obtainable, and measurements would take an hour or more. Thus, not only do these techniques take longer, they are unable to produce a density histogram.

The exemplary impaction densitometer 100 of FIGS. 1A-1E includes an impact chamber 110 configured to receive a particle. In certain exemplary embodiments, the impact chamber 110 optionally connects with a collection chamber 111 for returning sampled particles to a sample lot. A sealed collection port 112 optionally accesses the collection chamber 111, allowing the particles to be retrieved. The particles can be retrieved by pouring, vacuuming, or any other removal technique known to those of skill in the art.

The exemplary embodiment of FIGS. 1A-1E optionally includes an adjustable feeder 114, which can be automated. The embodiment shown includes a vibratory bowl similar to bowl feeding devices in automated feed of components in the semiconductor industry, although other feeders can be used without departing from the scope of the present subject matter. The exemplary feeder 114 vibrates such that particles climb an inner ramp (not shown), which ends at a feed port 116. In certain exemplary embodiments, a power supply (not shown) controls the intensity of the electromechanical vibrations of the feeder 114, and in certain embodiments is adjustable to control the vibration to obtain a desired particle feed rate. In this exemplary embodiment, an injector 118 connects the feeder 114 to the impact chamber 110.

While a vibratory bowl is used in this exemplary embodiment, other methods and apparatuses can be used to feed a particle into the chamber 111 without departing from the scope of the present subject matter. In certain exemplary embodiments, the impact chamber 110 is sealed. In a sealed impact chamber 110 an adjustable vacuum can be drawn, which pulls one or more particles into the impact chamber 110. As the impact chamber 110 is evacuated (to as much as −20 inches of mercury (−20 inHg) in certain examples), air enters the impact chamber 110 through the injector 118. Particles are picked up by the air flow and pulled through the injector 118 into the impact chamber 110 by the vacuum. Particle velocity in these exemplary embodiments is controlled by varying the vacuum level. Vacuum level is increased if a higher particle speed is desired, and decreased if a lower speed is desired. While a vacuum is used in this example, other methods can be used as well as or in addition to this without departing from the scope of the present subject matter. For example, particles can be dropped by gravity, pneumatically fed, electrostatically fed, electromagnetically fed, mechanically fed, electromechanically fed, and/or fed by other methods known to those of skill without departing from the scope of the present subject matter.

The exemplary embodiment shown further includes a beam generator 122 configured to emit a beam crossing a particle direction of travel within the impact chamber 110. In certain exemplary embodiments the beam is a laser beam. In other exemplary embodiments the beam is a light beam, an x-ray beam, an infrared beam, an electron beam, a gamma ray beam, an ultraviolet beam, and/or a combination of any of these beam types. In the exemplary embodiment shown, one or more windows 124 transparent to the beam enclose at least a portion of the impact chamber 110. The beam generator 122 is positioned such that the beam projects onto a detector 126. The detector 126 is outside impact chamber 110 in this exemplary embodiment, but need not be. In certain exemplary embodiments, the beam generator 122 is positioned such that the beam is perpendicular to the particle flight path past the particle injection point. The beam need not be perpendicular to the direction of travel, however, as other beam orientations (as much as ±20 degrees or more from perpendicular to the direction of travel) can be used without departing from the scope of the present subject matter.

In certain exemplary embodiments the beam is spread into a thin line or sheet. This can be done using at least one lens, at least one slit, at least one mirror, and/or at least one prism or other beam spreading techniques known to those of skill in the art. The beam is configured to be smaller than the particle passing through the beam such that chord distances can be calculated for a measured particle. In this exemplary embodiment, the beam is configured to be less than one tenth the width of the measured particle diameter, though other beam widths can be used. Although a laser beam is used in this example, other beams (such as electron, gamma, x-ray, microwave, acoustic, pneumatic, or other energy beams known to those of skill in the art) can be used without departing from the scope of the present subject matter.

In the exemplary embodiment of FIGS. 1A-1E the detector 126 is positioned a known distance from the beam and configured to receive the beam and convert a change in intensity of the received beam into an electrical signal. An impact sensor 130 (see, e.g., FIGS. 1D and 1E) is positioned a known distance from the beam. The distance from the beam to the impact sensor 130 is long enough to acquire the measurement data during the particle time of flight, but not so far that targeting error becomes a factor, or that particle throughput is reduced because of transit time to impact sensor 130. In certain embodiments this distance is adjustable. The particle passing through the beam blocks (shadows) at least a portion of the beam received by detector 126, causing a change in intensity in the output of detector 126. This change in intensity is converted into a signal used to determine at least one of the particle shape, size, and volume. In certain exemplary embodiments, the change in intensity is used to produce a signal attenuation curve (as shown, for example, in FIG. 2). The shape of the resulting signal attenuation curve yields data from which the diameter and shape of the particle can be calculated. Other techniques such as coherent diffraction imaging, acoustic imaging, stop action camera imaging, for example, can also be used to determine the object size and shape without departing from the scope of the present subject matter.

Figure 2:
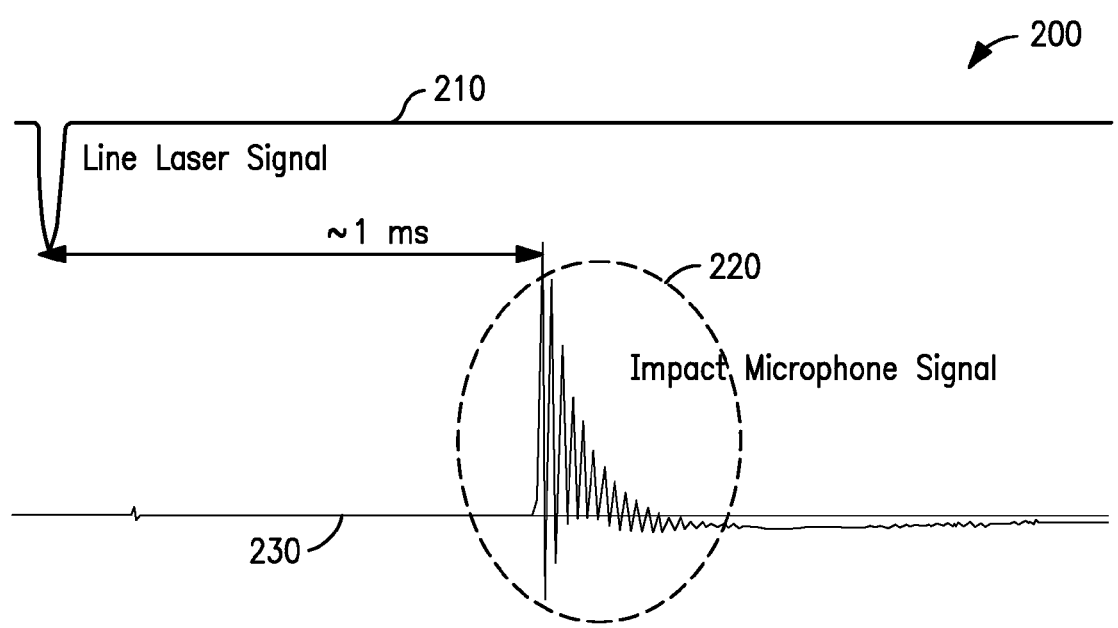
FIG. 2 illustrates an exemplary system response.

In this exemplary embodiment, the detector 126 includes a photodiode (not shown). The beam is projected onto the photodiode through a window 124, producing a voltage signal (as shown in FIG. 2, for example). A particle passing through the beam blocks a portion of the beam illuminating detector 126. This results in a decrease in the output of detector 126. In certain embodiments, this decrease triggers an automatic data acquisition module (not shown) which collects detector data. After crossing the beam, the particle strikes an impact sensor 130 positioned a known distance from the beam. The impact sensor 130 is configured to measure the particle momentum as a function of an impact energy transferred from the particle to the impact sensor 130. In this exemplary embodiment the impact sensor 130 is a microphone, though other sensors can be used without departing from the scope of the present subject matter. Examples include but are not limited to other acoustic measuring devices, piezoelectric sensors, piezoelectric transducers, accelerometers, ceramic microphones, condenser microphones, and MEMS devices.

FIG. 1E illustrates a block diagram of selected portions of an exemplary embodiment of an impaction densitometer 100. The exemplary embodiment includes a detector 126, an optional calibration unit 127, a size/volume calculator 129, an impact sensor 130, a velocity calculator 140, a mass calculator 150, and a density calculator 160. The relative configurations shown, as well as the number and arrangement of the connections shown are exemplary only, and not limited to what is shown. The items in this exemplary block diagram are implemented using software, firmware, hardware, and/or a combination thereof. In certain exemplary embodiments, calculations are implemented by electronic circuits hardwired to perform these calculations, and/or at least one microcontroller. Calculations may be implemented wholly or in part using software as an executable program in a non-transitory computer-readable medium executed by a general or speciallypurposed computer, such as a personal computer, workstation, minicomputer, or mainframe computer, generally referred to as a computer.

The computer may be windows-based and/or use any other operating system known to those of skill in the art. The computer at least partially implements the modules and elements described below with one or more computer processors, memory coupled to a memory controller, and one or more input and/or output (I/O) device(s) (peripheral(s)). Examples of the input/output controller include, but are not limited to, one or more buses or other wired or wireless connections. The input/output controller may have additional elements (omitted for simplicity) such as controllers, buffers (caches), drivers, repeaters, and receivers, to enable communications. Further, the device(s) may include address, control, and/or data connections to enable appropriate communications among the aforementioned components. When the systems and methods described herein are implemented in software, the methods are stored on any non-transitory computer readable medium for use by or in connection with any computer related system or method. The software in the non-transitory computer-readable medium may include one or more separate programs, and may be in the form of a source program, executable program (object code), script, or any other entity comprising a set of instructions to be performed.

In the exemplary block diagram of FIG. 1E, the detector 126 is configured to identify the particle shape and/or size. These particles need not be the same shape or size. Particle shapes include but are not limited to spherical, rod shaped, and ellipsoidal. Other shapes can be used without departing from the scope of the present subject matter. In these exemplary embodiments, the detector 126 detects the particle shape and calculates particle volume based at least on the shape detected and the attenuation of the received beam. The detector 126 can measure multiple shapes as well as particles of different sizes for each shape. Particle size is calculated at least in part by calibrating the beam attenuation on the y-axis of curve 210 (see, e.g., FIG. 2) into distance measurement units and integrating the area under the entire attenuation curve with the calculated distance traveled per data channel collected measurement using particle velocity and data acquisition rate. Particle shape is obtained by analyzing the shape and symmetry of the attenuation curve.

The exemplary impaction densitometer 100 embodiment of FIG. 1E optionally includes a calibration unit 127. The calibration unit 127 is configured to calibrate the output of detector 126. To calibrate the output of detector 126, one or more objects of known size and/or shape are passed through the beam. The attenuation of the output of detector 126 resulting from the known object passing through the beam is measured, and set as a baseline output to use with determining a size and/or shape of an unknown object size/volume by calculator 129. The extent that the output of detector 126 varies from one or more of these baselines is used to calculate a size and/or shape of the unknown object using the techniques described above. The calibration unit 127 may also be used to establish a baseline of the output of mass calculator 150. An object of known mass is impacted with impact sensor 130, and the output of impact sensor 130 from the impact of the object of known mass is used to establish a baseline mass signal for calculator 150. Mass is calculated based at least in part on the amount that an output from impact sensor 130 varies from the output from the impact with the object of known mass.

In the exemplary embodiment of FIG. 1E, the velocity calculator 140 is configured to calculate a particle velocity based on a time it takes the particle to pass through the beam and strike the impact sensor 130. In this embodiment, velocity is calculated from the time it takes the particle to break the plane of the beam to the initial strike on the impact sensor 130, located a known distance from the beam. This time of flight is divided into the known distance between the beam and the impact sensor 130 to calculate particle velocity. The impaction densitometer 100 of FIG. 1E further includes a mass calculator 150 configured to calculate particle mass as a function of particle momentum and velocity. Since momentum is the product of mass times velocity, the particle mass is obtained using the momentum measured from the impact sensor 130 and the velocity calculated by the velocity calculator 140. The mass is calculated by dividing particle momentum by particle velocity. Other techniques for obtaining mass can also be used without departing from the scope of the present subject matter. The exemplary embodiment of FIG. 1E also includes a density calculator 160 configured to calculate a particle density as a function of the particle mass and volume. In this exemplary embodiment, density is calculated by dividing the particle mass by the particle volume.

FIG. 2 illustrates an exemplary system response 200. Beam attenuation appears as a negative peak in the voltage vs. time plot of the detector 126, as shown by the first trace 210. The particle impact on the impact sensor 130 produces a "ringing" signal 220, the height of which is proportional to the impact energy, and the frequency of which is characteristic of the resonance frequency of the impact sensor 130, an example of which is shown as the second trace 230. In certain exemplary embodiments, the impact sensor 130 includes a dynamic microphone having diaphragm, electromagnet, and coil (not shown) configured to generate a signal from the acoustic energy generated by the impact. In certain exemplary embodiments, the impact sensor 130 is positioned opposite the injector 118, but it need not be. In certain exemplary embodiments, the combination of a heavy particle and high velocity can push the impact sensor 130 signal beyond the hardware's maximum input voltage. In these exemplary embodiments, larger particles are typically run at lower vacuum levels of −5 to −10 inches of mercury (−5 to −10 inHg) to reduce the energy of the particle by reducing its velocity. Conversely, smaller particles typically require higher vacuum levels up to −20 inches of mercury (−20 inHg) to obtain a velocity which produces an impact of sufficient energy to produce a signal exceeding the signal to noise ratio of the impact sensor 130, but low enough that the impact does not cause any damage.

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:
1. An impaction densitometer, comprising:
a chamber configured to receive a particle;
a beam generator configured to emit a beam crossing a particle direction of travel within the chamber;
a detector configured to receive the beam and convert a change in intensity of the received beam, resulting from the particle passing through the beam, into an electrical signal corresponding to a particle volume;
an impact sensor positioned a known distance from the beam and configured to measure a particle momentum as a function of an impact energy transferred from the particle to the impact sensor;

a velocity calculator configured to calculate a particle velocity based on a time it takes the particle to pass through the beam and strike the impact sensor;

a mass calculator configured to calculate a particle mass as a function of the particle momentum and velocity; and a density calculator configured to calculate a particle density as a function of the particle mass and volume.

2. The impaction densitometer of claim 1, further comprising an adjustable vacuum generator connecting with the chamber.

3. The impaction densitometer of claim 1, further comprising an adjustable feeder configured to feed the particle into the chamber.

4. The impaction densitometer of claim 3, further comprising an injection needle connecting the adjustable feeder to the chamber.

5. The impaction densitometer of claim 1, further comprising a beam spreader configured to spread the beam into a sheet.

6. The impaction densitometer of claim 5, wherein the beam spreader is selected from the group consisting of at least one lens, at least one slit, at least one mirror, and at least one prism.

7. The impaction densitometer of claim 1, wherein the beam generator is further configured to emit the beam perpendicular to the particle travel direction.

8. The impaction densitometer of claim 1, wherein the detector includes a photodiode configured to produce a signal attenuation curve containing data on particle diameter and shape.

9. The impaction densitometer of claim 1, wherein the impact sensor is a microphone.

10. The impaction densitometer of claim 1, wherein the impact sensor is configured to produce an impact signal proportion to an impact energy generated by the particle striking the impact sensor.

11. The impaction densitometer of claim 1, further comprising a data acquisition module configured to acquire particle data upon detection of the change in beam intensity.

12. A method of particle measurement, comprising the steps of:

passing a particle through a beam;

measuring a change in intensity of the beam resulting from the particle passing through the beam;

calculating a particle volume based on the change in beam intensity;

impacting the particle at a known distance from the beam;

measuring an impact energy of the particle;

calculating a particle momentum as a function of the particle impact energy;

calculating a particle velocity as a function of a time it takes the particle to impact after travelling the known distance from the beam;

calculating a particle mass as a function of the particle momentum and velocity; and calculating a particle density as a function of the particle mass and volume.

13. The method of claim 12, further comprising the step of creating an adjustable vacuum within the chamber.

14. The method of claim 12, further comprising the step of feeding multiple particles into the chamber.

15. The method of claim 14, further comprising the step of calculating at least 10 particle densities per second.

16. The method of claim 15, further comprising the step of preparing a histogram of at least one of a plurality of particle densities and a plurality of particle sizes.

17. The method of claim 12, further comprising the step of orienting the beam perpendicular to the particle travel direction.

18. The method of claim 12, further comprising the step of spreading the beam into a sheet.

19. The method of claim 12, further comprising the step of producing a signal attenuation curve containing data on particle diameter and shape.

20. A computer program product comprising a non-transitory computer readable medium having stored thereon computer executable instructions that when executed causes the following steps to be performed, the steps comprising:

passing a particle through a beam;

measuring a change in intensity of the beam resulting from the particle passing through the beam;

calculating a particle volume based on the change in beam intensity;

impacting the particle at a known distance from the beam;

measuring an impact energy of the particle;

calculating a particle momentum as a function of the particle impact energy;

calculating a particle velocity as a function of a time it takes the particle to impact after passing through the known distance from the beam;

calculating a particle mass as a function of the particle momentum and velocity; and calculating a particle density as a function of the particle mass and volume.

\* \* \* \* \*